United States Patent
Cooper et al.

(10) Patent No.: US 12,329,401 B2
(45) Date of Patent: Jun. 17, 2025

(54) INSTRUMENT SHAFTS WITH RELIEF FEATURES, AND RELATED DEVICES, SYSTEMS, AND METHODS

(71) Applicant: INTUITIVE SURGICAL OPERATIONS, INC., Sunnyvale, CA (US)

(72) Inventors: Thomas G. Cooper, Menlo Park, CA (US); Isabelle Tonnesen Heye, San Francisco, CA (US); Thomas Welch Brown, Santa Clara, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 258 days.

(21) Appl. No.: 17/784,317

(22) PCT Filed: Dec. 11, 2020

(86) PCT No.: PCT/US2020/064538
§ 371 (c)(1),
(2) Date: Jun. 10, 2022

(87) PCT Pub. No.: WO2021/119444
PCT Pub. Date: Jun. 17, 2021

(65) Prior Publication Data
US 2023/0039267 A1 Feb. 9, 2023

Related U.S. Application Data

(60) Provisional application No. 62/947,079, filed on Dec. 12, 2019.

(51) Int. Cl.
*A61B 17/29* (2006.01)

(52) U.S. Cl.
CPC ...... *A61B 17/29* (2013.01); *A61B 2017/2901* (2013.01); *A61B 2017/2905* (2013.01); *A61B 2017/2908* (2013.01)

(58) Field of Classification Search
CPC ............ A61B 17/29; A61B 2017/2901; A61B 2017/2905; A61B 2017/2908
See application file for complete search history.

(56) References Cited

U.S. PATENT DOCUMENTS

| 6,273,876 B1 * | 8/2001 | Klima ............... | A61M 25/0051 604/264 |
| 2005/0043711 A1 * | 2/2005 | Corcoran .......... | A61M 25/0054 604/523 |

(Continued)

FOREIGN PATENT DOCUMENTS

JP 2014000436 A 1/2014

OTHER PUBLICATIONS

International Search Report and Written Opinion for Application No. PCT/US2020/064538, mailed on Apr. 9, 2021, 9 pages.

(Continued)

*Primary Examiner* — Tan-Uyen T Ho
*Assistant Examiner* — Cherie M Poland
(74) *Attorney, Agent, or Firm* — Jones Robb, PLLC

(57) ABSTRACT

An instrument includes a tubular shaft, an end effector coupled to a distal end portion of the tubular shaft, and a relief feature extending circumferentially along a wall of the shaft and along at least a portion of a length of the shaft. The relief feature defines flexural members on opposing sides of the relief feature. The flexural members can move relative to one another in response to bending the shaft. The flexural members can engage one another on one or both of tension and compression sides of the shaft on the condition the shaft is bent to an angle within a predetermined range of bend (Continued)

angles. Systems and methods relate to instruments including such shafts.

19 Claims, 18 Drawing Sheets

(56) References Cited

U.S. PATENT DOCUMENTS

| | | |
|---|---|---|
| 2007/0135826 A1* | 6/2007 | Zaver ............... A61B 17/12022 |
| | | 606/157 |
| 2010/0151161 A1 | 6/2010 | Da Rolo |
| 2012/0143175 A1* | 6/2012 | Hermann ........... A61B 17/3207 |
| | | 606/1 |
| 2014/0001231 A1 | 1/2014 | Shelton, IV et al. |
| 2017/0071688 A1 | 3/2017 | Cohen et al. |
| 2019/0239967 A1 | 8/2019 | Ragosta et al. |
| 2019/0365202 A1 | 12/2019 | Larkin et al. |

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
Extended European Search Report for Application No. EP20900161.9, mailed on Nov. 28, 2023, 11 pages.

* cited by examiner

INSTRUMENT SHAFTS WITH RELIEF FEATURES, AND RELATED DEVICES, SYSTEMS, AND METHODS

CROSS-REFERENCE TO RELATED APPLICATIONS

This application is a U.S. national stage application under 35 U.S.C. § 371(c) of International Application No. PCT/US2020/064538, which claims the benefit of priority to U.S. Provisional Application No. 62/947,079 (filed Dec. 12, 2019), titled "INSTRUMENT SHAFTS WITH RELIEF FEATURES, AND RELATED DEVICES, SYSTEMS, AND METHODS," the entire contents of each of which are incorporated by reference herein.

TECHNICAL FIELD

Aspects of the present disclosure relate to instrument shafts with relief features that increase flexibility of the shaft without increasing rotational backlash, and related systems and methods.

INTRODUCTION

Instruments, such as surgical or industrial instruments, can have a variety of configurations to perform various types of procedures. Some instrument systems are configured for minimally invasive surgery. In some such systems, each individual instrument includes an end effector at a distal end of a shaft for positioning at a site at which a procedure will take place. Such instruments may include transmission mechanisms positioned at a proximal end of the shaft and configured to mount the instrument to a manipulator system, such as a teleoperated (e.g., computer-controlled) manipulator system a manipulator system configured for manual operation. Transmission mechanisms of these tools can include numerous mechanical subsystems that receive mechanical inputs, e.g., from the manipulator system or manually via a user, and generate movement and actuation of the instrument, such as operation of the end effector, articulation of one or more joints of the shaft proximal of the end effector, shaft roll, and other operations or movements. Other instruments in medical, industrial, or other use applications can include shafts and associated components with similar construction and function.

For various reasons, it may be desirable to provide shafts of such instruments with a degree of flexibility. For example, in a system with multiple instruments like those described above being configured to at a single location to carry out a procedure, the end effectors at the distal ends of the instrument shafts must be in parallel and in close proximity. Because of the potentially large number of mechanical components and subsystems contained in the associated transmission mechanisms at proximal ends of the shafts, the size of the transmission mechanisms constrains how closely together the proximal ends of the shafts can be positioned. Allowing the shaft some bending flexibility can enable the distal ends to be in close proximity while allowing sufficient clearance for the transmission mechanisms at the proximal end. In other applications and system architectures, a degree of flexibility may be desired for other reasons. But shafts made from flexible materials can behave in undesirable ways for certain applications, such as exhibiting higher axial compliance than desirable.

There exists a need to provide an instrument shaft that exhibits a relatively high compliance in bending while also exhibiting relatively high axial and rotational stiffness.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary aspect of the present disclosure, an instrument comprises a tubular shaft, an end effector coupled to a distal end portion of the tubular shaft, and a relief feature extending circumferentially along a wall of the shaft and along at least a portion of a length of the shaft, the relief feature defining flexural members on opposing sides of the relief feature. The flexural members move relative to one another in response to bending the shaft. The flexural members engage one another on one or both of tension and compression sides of the shaft on the condition the shaft is bent to an angle within a predetermined range of bend angles.

In accordance with at least another exemplary aspect of the present disclosure, a method of installing an instrument in a manipulator system includes bending a shaft of the instrument to an angle within a range of predetermined bend angles. During the bending, flexural members defined by a relief feature in a wall of the shaft move relative to one another, and the flexural members engage one another on one or both of a tension side of the shaft and a compression side of the shaft when the shaft is bent to the angle within the range of predetermined bend angles.

In accordance with yet another exemplary aspect of the present disclosure, a method of making an instrument shaft includes forming a relief feature along a wall of a tubular shaft. The relief feature defines flexural members on opposing sides of the relief feature of the tubular shaft body. The flexural members are configured to engage one another on one or both of tension and compression sides of the shaft on the condition the shaft is bent to an angle within a predetermined range of bend angles.

In accordance with yet another exemplary aspect of the present disclosure, an instrument includes a tubular shaft and an end effector coupled to a distal end portion of the tubular shaft. A relief feature extends circumferentially along a wall of the shaft and along at least a portion of a length of the shaft. The relief feature defines flexural members on opposing sides of the relief feature. The flexural members are movable relative to one another on the condition that the shaft is bent to an angle below a predetermined range of bend angles. On the condition that shaft is bent to an angle within a predetermined plurality of bend angles, the flexural members engage one another and prevent one or both of twisting and axial movement of the flexural members relative to one another.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure and are incorporated in and constitute a part of this specification. The drawings illustrate one or more exemplary embodiments of the present teachings and, together with the description, explain certain principles and operation. In the drawings.

DETAILED DESCRIPTION

Figure 1:
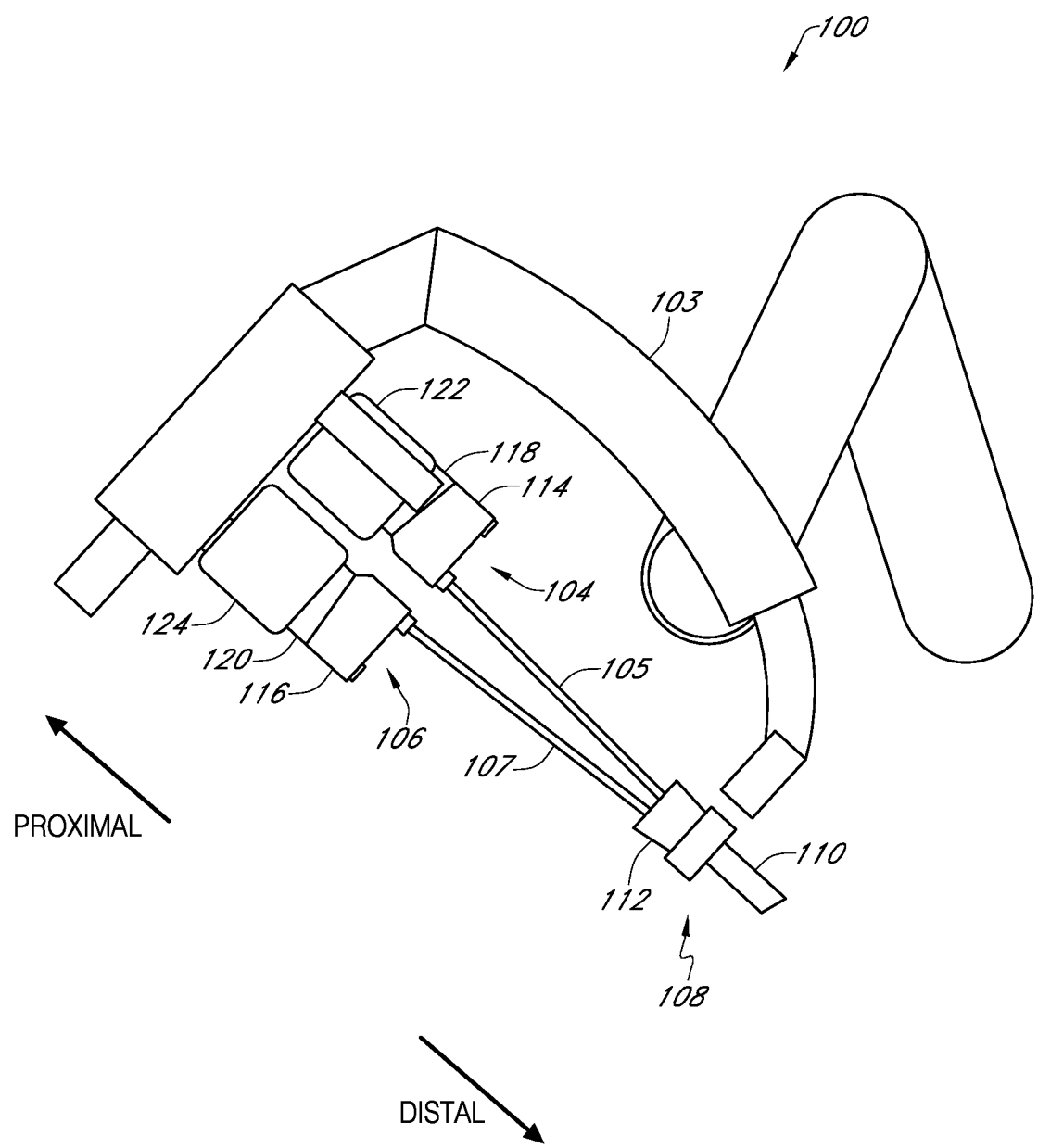
FIG. 1 is a partial schematic view of an embodiment of a manipulator arm of a manipulating system of a computer-assisted surgical system with two instruments in an installed position.

The present disclosure contemplates various exemplary embodiments of shafts for instruments that include relief features that impart lateral flexibility (bending) to the shaft while maintaining relatively high axial stiffness and minimizing (e.g., reducing or eliminating) rotational backlash to allow controlled roll of the shaft. Such shafts can be made from relatively stiff materials, such as metal alloys, polymers, or other materials to provide the desired stiffness and durability under the specific conditions under which the instrument is used, while the relief features impart flexibility allow some degree of bending. For example, in one use scenario, such shafts can facilitate coupling the instrument to a manipulator in a use configuration. Such shafts can be used in any other situation where a degree of shaft flexibility is desired.

In one embodiment of the disclosure, a shaft includes a relief feature that extends circumferentially around at least a portion of the shaft and extends at least partially through a wall thickness of the shaft, thereby defining adjacent portions of the shaft. The relief feature defines complementary interlocking engagement members that engage one another at differing locations depending on whether they are located on a tension side or a compression side of the shaft when the shaft having the relief feature is bent to a predetermined angle. Engagement between the complementary interlocking engagement members at the predetermined bend angle minimizes (e.g., reduces or eliminates) rotational backlash in the shaft (e.g., due to twisting of the shaft about a longitudinal axis resulting in movement of portions of the shaft with respect to other portions of the shaft) and ensures the shaft maintains axial stiffness and rotational stiffness when the predetermined bend angle is achieved.

Shafts having such relief features can facilitate positioning of associated instruments as desired, such as in a multiple-instrument configuration as discussed above and below in connection with FIG. 1. Additionally, the relief features provide the desired degree of bending to facilitate such uses while maintaining rotational and axial compliance at a level generally equal to the characteristics exhibited by the material of the shaft. Thus, shafts with relief features according to embodiments of the present disclosure are able to withstand reaction forces resulting from actions such as actuating an end effector coupled to the shaft, rotating the shaft in a roll motion, or other movements, with reduced deflection as compared to conventional shafts exhibiting a similar degree of flexibility.

In the description below, shafts according to exemplary embodiments of the present disclosure are disclosed and described in connection with a manipulator system having multiple instruments. However, shafts having the features disclosed herein can be used in any application for which flexibility of the shaft for positioning of the shaft is desired, without significantly compromising axial and rotational stiffness of the shaft.

Referring now to FIG. 1, a schematic view of a manipulator system 100 including a manipulator arm 103 with two surgical instruments 104, 106 in an installed position is shown. The surgical instruments 104, 106 can generally correspond to instruments discussed below, such as instrument 204 disclosed in connection with FIG. 2. For example, the embodiments described herein may be used with a DA VINCI SP® Surgical System, commercialized by Intuitive Surgical, Inc. of Sunnyvale, California. The schematic illustration of FIG. 1 depicts only two surgical instruments for simplicity, but more than two surgical instruments may be mounted in an installed position at a manipulating system as those having ordinary skill in the art are familiar with. Each of surgical instruments 104 and 106 includes an instrument shaft 105 and 107 respectively that, at a distal end, has a moveable end effector or an endoscope, camera, or other imaging or sensing device, and may or may not include a wrist mechanism (not shown) to control the movement of the distal end.

In the embodiment of FIG. 1, the distal end portions of the surgical instruments 104, 106 are received through a single port structure 108 to be introduced into the patient. As shown, the port structure includes a cannula 110 and an instrument entry guide 112 inserted into the cannula 110. Individual surgical instruments 104, 106 are inserted into the entry guide 112 and through the cannula 110 to reach a surgical site.

Transmission mechanisms 114, 116 (which may generally correspond to force transmission mechanism 102 disclosed in connection with FIG. 1A) are disposed at a proximal end of each instrument shaft 105, 107 and connect to drive assemblies 122, 124 through a sterile adaptor 118, 120. Drive assemblies 122, 124 contain a variety of internal mechanisms (not shown) that are controlled by a controller (e.g., at a control interface of the manipulator system) to respond to input commands at a user control system of the manipulator system 100 to transmit forces to the transmission mechanisms 114, 116 to actuate surgical instruments 104, 106.

As shown in FIG. 1, the instrument shafts 105, 107 are positioned close to one another as they enter the entry guide 112, and gradually diverge from one another in the proximal direction, i.e., toward the transmission mechanisms 114, 116 and the drive assemblies 122, 124. Due to this divergence from one another, the instrument shafts 105, 107 each assume a slight S-shaped bend, as discussed in greater detail below.

Figure 10A:
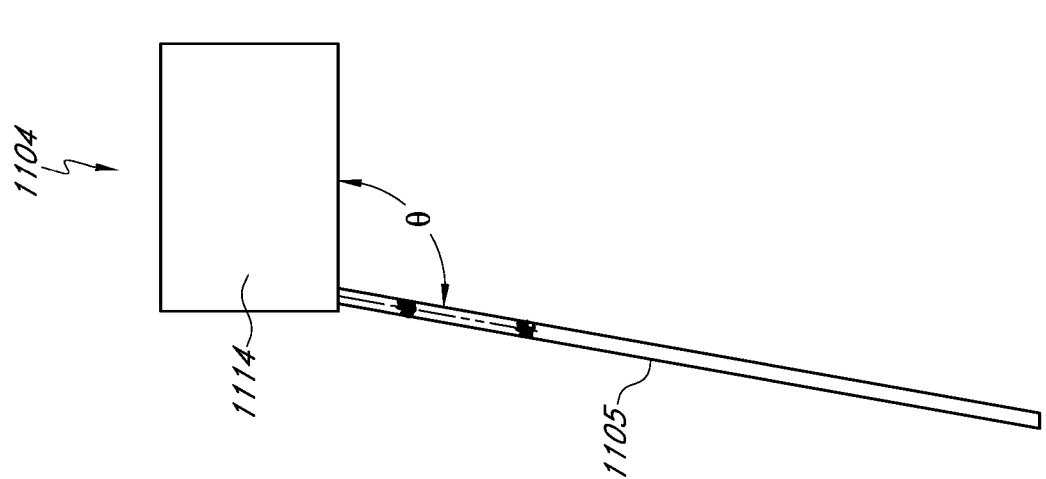
FIG. 10A is a side view of an instrument according to the present disclosure in an uninstalled position.
Figure 10B:
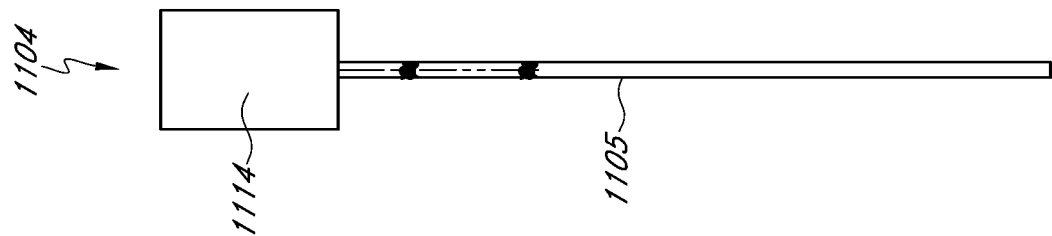
FIG. 10B is a front view of the instrument of FIG. 10A.
Figure 10D:
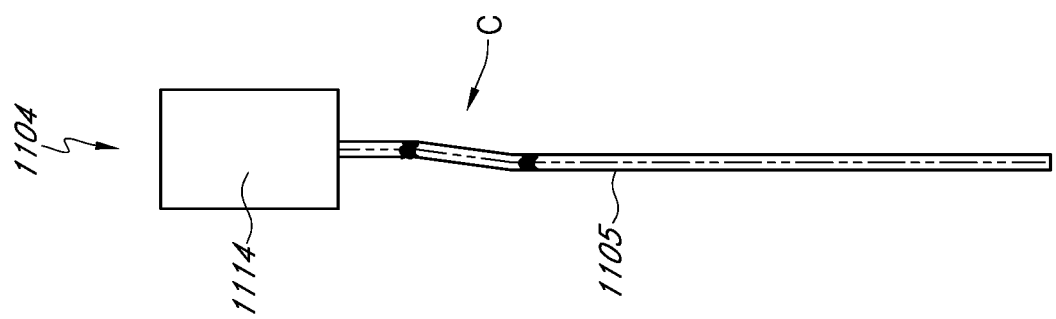
FIG. 10D is a front view of the instrument in the installed position of FIG. 10C.
Figure 10C:
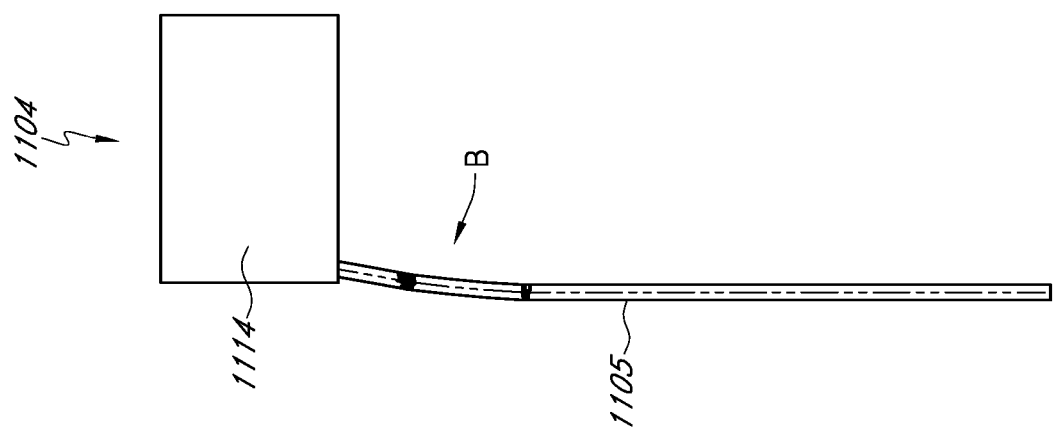
FIG. 10C is a side view of the instrument of FIGS. 10A and 10B in an installed position.

In some exemplary embodiments of the present disclosure, the instrument shafts 105, 107 may exhibit one or more compound bends when the instruments are in the installed position in the manipulator system 100. Further, the instrument shafts 105, 107 can exhibit simple or compound bends in one or more different bending planes. For example, referring now to FIGS. 10A-10D, various views of an instrument 1104 are shown. FIGS. 10A and 10C are side views (similar to the view of instrument 204 FIG. 2) of the instrument 1104, and FIGS. 10B and 10D are end views of instrument 1104 (similar to the views of the instruments 104, 106 in FIG. 1). FIGS. 10A and 10B represent instrument 1104 according to the present disclosure in an uninstalled state. In this embodiment, a shaft 1105 of the instrument 1104 emanates from the transmission mechanism 1114 at a non-orthogonal angle θ. As shown in FIGS. 10A and 10B, in an uninstalled position, the shaft 1105 emanates generally straight from the transmission mechanism 1114. In FIG. 10C, it can be seen that the shaft 1105 assumes a gradual, arc-shaped bend B in the installed position as it lies in the plane of FIG. 10C. The shaft 1105 assumes a compound bend C in the plane of FIG. 10D. The compound bend of the shaft 1105 shown in FIG. 10D enables multiple instruments (such as instruments 104, 106 in FIG. 1) to be mounted parallel to one another and compensates for the offset required between the transmission mechanism 1114 and the entry guide (FIG. 2) to enable multiple instruments (e.g., instruments 104 and 106 in FIG. 2) to be inserted through the same entry guide (e.g., entry guide 112 in FIG. 2). Other combinations of simple and/or compound bends in one or more bending planes are within the scope of the present disclosure. Embodiments of the present disclosure provide shafts with features that facilitate assumption of the desired bend geometry, while maintaining a desired level of axial and rotational stiffness in the shaft.

The embodiments described herein are not limited to the embodiment of FIG. 1, and various other teleoperated, computer-assisted manipulator configurations may be used with the embodiments described herein. The diameter or diameters of an instrument shaft, wrist mechanism, and end effector are generally selected according to the size of the cannula with which the instrument will be used and depending on the surgical procedures being performed. Other configurations of manipulating systems that can be used in conjunction with the present disclosure can use several individual manipulator arms. In addition, individual manipulator arms may include a single instrument or a plurality of instruments. Further, as discussed above, an instrument may be a surgical instrument with an end effector or may be a camera instrument or other sensing instrument utilized during a surgical procedure to provide information, (e.g., visualization, electrophysiological activity, pressure, fluid flow, and/or other sensed data) of a remote surgical site.

Figure 2:
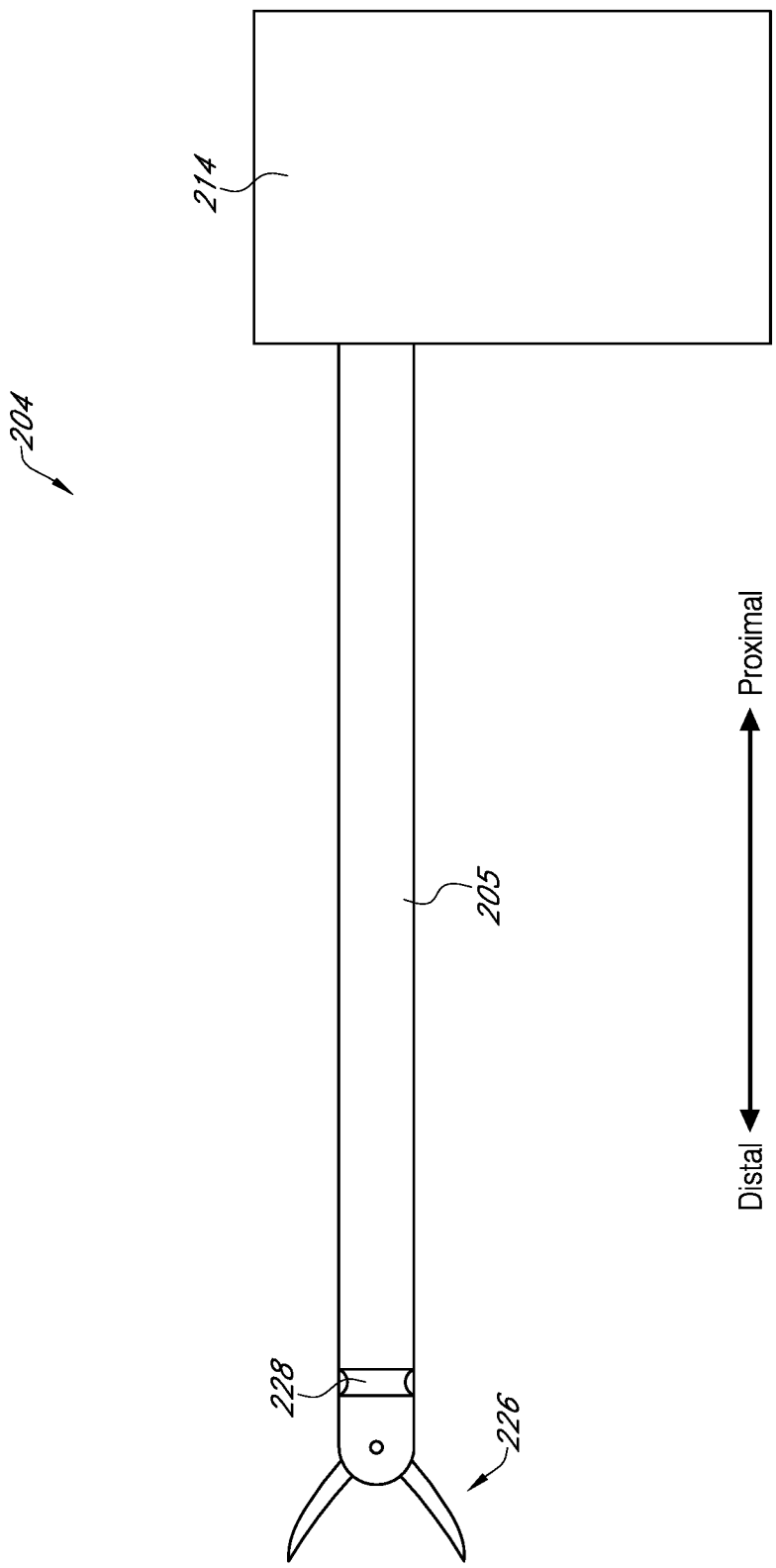
FIG. 2 is a schematic view of an exemplary embodiment of an instrument according to an embodiment of the present disclosure.

Referring now to FIG. 2, a schematic side view of an embodiment of an instrument 204 (such as, for example, surgical instrument 104 or 106) is shown. While aspects of the present disclosure are discussed in the context of surgical instruments, embodiments of the present disclosure can be used with various instruments used in surgical or non-surgical procedures. For example, such instruments include those used for diagnosis, therapy, and sensing, including, for example, imaging instruments such as endoscopes and other imaging instruments. Accordingly, surgical instruments as used herein encompasses a variety of instruments used in surgical, diagnostic, and therapeutic applications. In addition, aspects of the disclosure can have non-surgical applications, such as in other remotely-actuatable instruments for inspection and other industrial uses, general robotic uses, manipulation of non-tissue work pieces, etc.

The instrument 204 includes a transmission mechanism 214 at a proximal end of a shaft 205. In an exemplary embodiment, the transmission mechanism 214 is configured to interface with a manipulating system, such as manipulating system 100 discussed in connection with FIG. 1. Alternatively, the transmission mechanism 214 can be configured to be operated manually such as for a manual, laparoscopic instrument.

An end effector 226 is coupled to a distal end portion of the shaft 205. The end effector 226 can be coupled directly to the shaft 205 or may be coupled to the shaft 205 by a wrist 228, which may include one or more articulatable joints to impart one or more degrees of freedom of movement to the end effector 226 relative to the shaft 205 (for example, to move the wrist 228 in one or more of pitch and yaw).

Operation of the end effector 226 can be controlled by manipulation of the transmission mechanism 214, either manually or through drives of a manipulating system (e.g., manipulating system 100 shown in FIG. 1). The transmission mechanism 214 includes various mechanical and/or electromechanical devices that transmit motion, energy, and/or signals, e.g., from the manipulating system, or from inputs at the transmission mechanism 214 operable by a user, to the end effector 226. While the end effector 226 shown in FIG. 2 comprises a pair of opposing jaw members, other end effector configurations, such as staplers, clip appliers, ligation tools, and other tools are considered within the scope of this disclosure.

As noted above, the instrument 204 may also include wrist 228 to facilitate orienting the end effector 226. For example, the wrist 228 may comprise one or more articulating joints disposed at a distal end portion of the shaft 205 and couple the end effector 226 to the shaft 205 so that the end effector 226 moves relative to the shaft 205 in one or more degrees of freedom.

Figure 3:
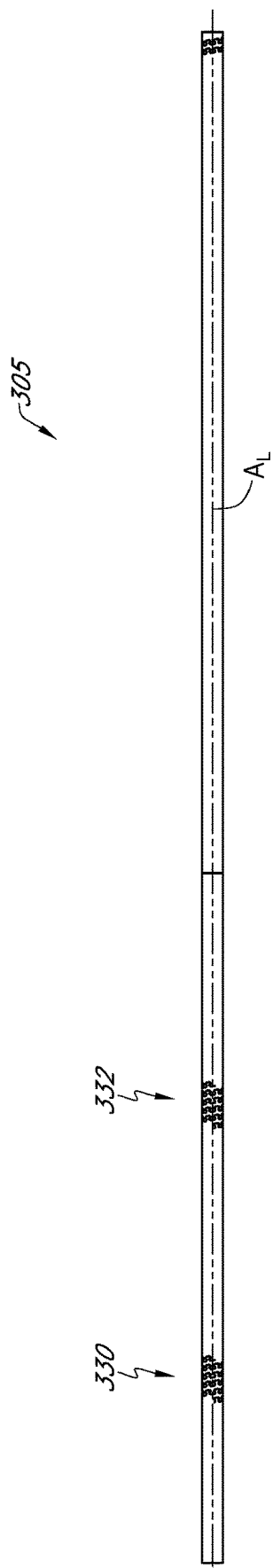
FIG. 3 is a side view of an instrument shaft according to an exemplary embodiment of the present disclosure.

Referring now to FIG. 3, an instrument shaft 305 according to an embodiment of the disclosure is shown. The instrument shaft 305 comprises a tubular structure that includes one or more portions that have relief features that impart flexibility to the shaft 305 while minimizing (e.g., reducing or eliminating) a corresponding increase in axial or rotational compliance. As used herein, the term "tubular," "tube," and variants thereof refer to a structure with a lateral wall defining an interior hollow portion. The cross-sectional shape of the lateral wall (i.e., shape in a plane normal to the longitudinal axis) is not limited and can be, for example, circular, ovoid, elliptical, polygonal, combinations thereof, or any other shape. In addition, the cross-sectional shape of the lateral wall may be constant along the length of the shaft or may vary along the length of the shaft. The one or more portions can be positioned along the shaft 305 at locations that enable the shaft 305 to assume a slight S-shaped bend configuration (as shown in FIG. 1) when the shaft 305 and corresponding instrument are installed in a manipulator system, such as manipulator system 100 discussed in connection with FIG. 1.

For example, in the embodiment of FIG. 3, the shaft 305 includes a first portion 330 and second portion 332 each with features (e.g., relief features) configured to impart flexibility to the shaft 305. The longitudinal position of the first portion 330 and second portion 332 shown in FIG. 3 is exemplary only, and such portions can be at any location along the length of the shaft 305. Further, the shaft 305 can optionally include only one portion, or three or more portions, with relief features. The number of portions, longitudinal extent of the portions, and location of the portions having relief features can be chosen based on a total deflection required for the specific configuration of the surgical instrument and manipulator system. For example, if a relatively greater the amount of deflection is desired, a greater the number and/or a greater longitudinal extent (i.e., length) of the portions can be utilized. In some embodiments, the shaft 305 can optionally include relief features along a majority of its length.

The relief features can comprise a relief formed through a wall thickness of the tubular structure of the shaft 305. For example, the relief features can comprise negative features formed completely through the thickness of the shaft wall thickness. In some exemplary embodiments, such negative features can extend generally around the circumference of the shaft 305 and can have a generally helical pattern such that the shaft remains a single piece. In other exemplary embodiments, the negative features can extend circumferentially and separate the shaft 305 into discrete, but interlocking, pieces. The relief features can have a configuration that minimizes (e.g., reduces or eliminates) axial and rotational compliance of the shaft when the shaft is in a bent position, as discussed in greater detail in connection with FIGS. 4 and 5A-5C.

Figure 4:
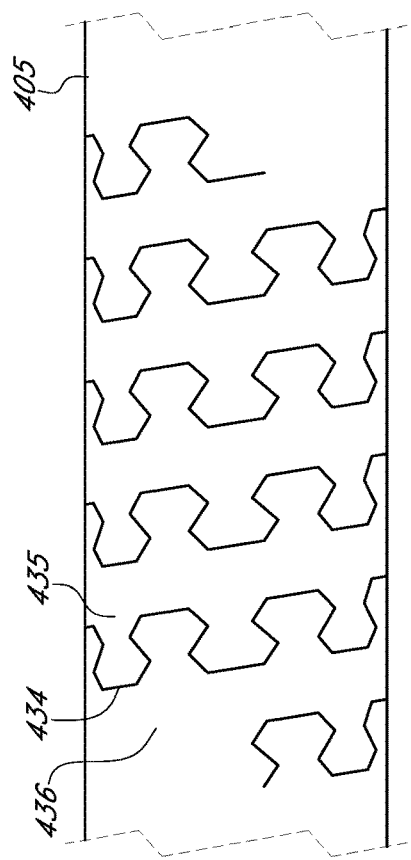
FIG. 4 is a partial, enlarged view of the instrument shaft of FIG. 3.
Figure 4:
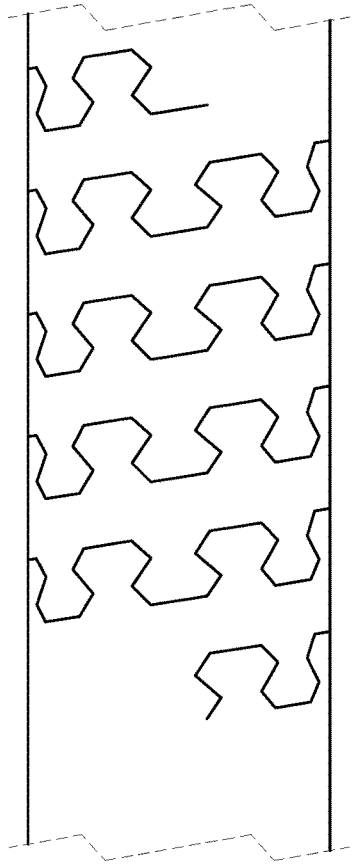

Referring now to FIG. 4, an enlarged view of a portion (such as portion 330 or 332) of a shaft 405 having a relief feature 434 is shown. The relief feature 434 extends through the wall of the shaft 405 and around the circumference of the shaft in a generally helical pattern as shown in FIG. 4. The relief feature 434 defines opposite sides 435 and 436 of the shaft 405. In the embodiment of FIG. 4, the opposite sides 435 and 436 represent adjacent helical wraps of the shaft 405, and thus the opposite sides 435 and 436 can be different portions of the same individual component, i.e., the shaft 405, which remains a single piece since the relief feature 434 is formed helically. In other embodiments, for example, embodiments in which the relief feature 434 is formed as a series of concentric, non-helical reliefs, the opposite sides 435 and 436 could be entirely separate components. Further, portions of the shaft 405 separated by relief features, such as relief features 434, 634 (FIG. 6,) 834 (FIG. 8), 934 (FIG. 9), and 1134 (FIG. 11), can be referred to as flexural members, because the relief feature 434 can impart additional flexibility to the shaft 405 as discussed herein.

The relief feature also defines interlocking features configured to minimize (e.g., reduce or eliminate) axial and rotational compliance (such as rotational backlash) introduced by the relief feature 434. For example, such features can be configured to mechanically interlock to impart axial and rotational stiffness to the shaft 405 when the shaft 405 is bent to a predetermined angle. As shown in FIG. 4, the relief feature 434 defines a repeating, interlocking pattern in the shaft 405 with complementary interlocking engagement members 438. The interlocking features serve to prevent rotational compliance (e.g., backlash due to twisting of the shaft about a longitudinal axis resulting in movement of portions of the shaft with respect to other portions of the shaft) when the shaft is subjected to a rotational torque.

Figure 5A:
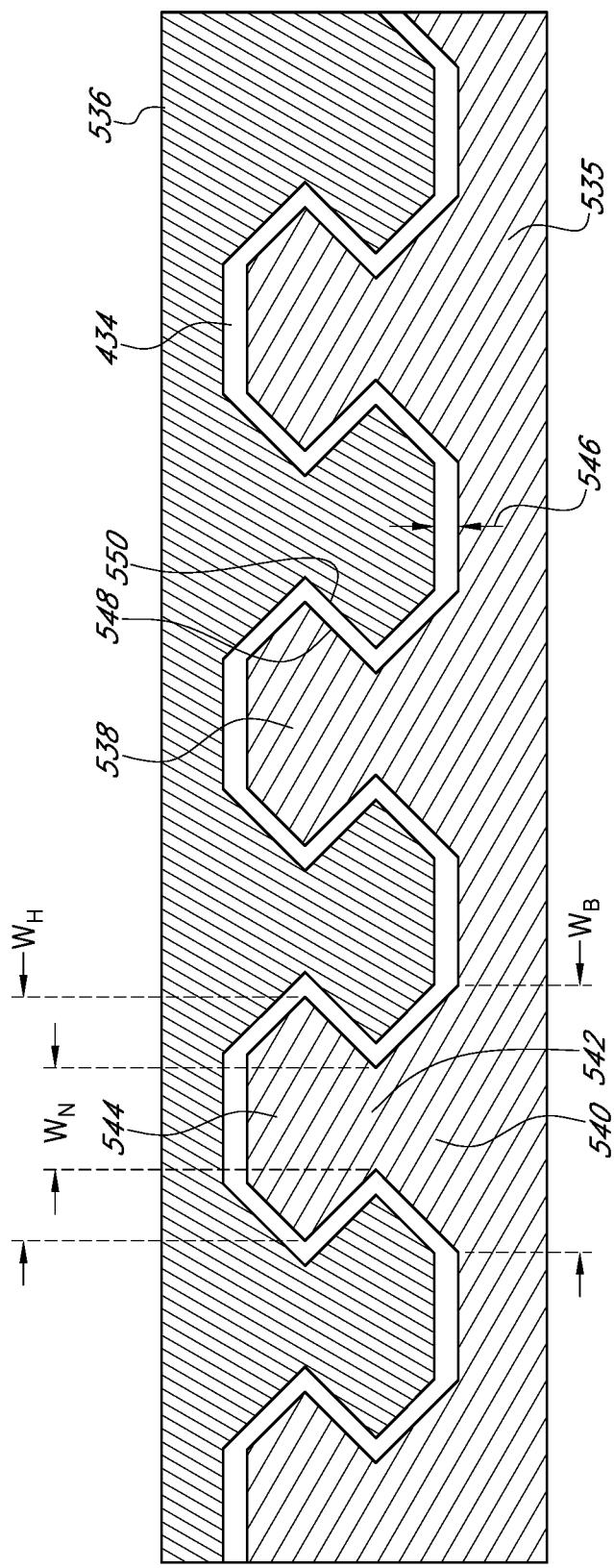
FIG. 5A is a partial enlarged side view showing the relief features of the instrument shaft of FIG. 4 in a neutral configuration.

Referring now to FIG. 5A, an enlarged view of the relief feature 434 is shown. As shown in the embodiment of FIG. 5A, the relief feature 434 defines opposite sides 535 and 536 of the shaft, each having complementary interlocking engagement members 538 in the shaft (such as shaft 405 in FIG. 4). As shown in FIG. 5A, each of the complementary interlocking engagement members 538 has a base 540 with a width $W_B$, a neck 542 with a width $W_N$, and a head portion 544 with a width $W_H$. The width $W_B$ of the base 540 and the width $W_H$ of the head portion 544 are greater than the width $W_N$ of the neck 542. Each of the complementary interlocking engagement members includes corresponding features, and, as shown in FIG. 5A, the complementary interlocking engagement members are configured such that they form interlocking components separated by a gap 546. The gap 546 can be a result of a manufacturing process, such as a kerf left by a cutting process (such as, for example, laser cutting, water jet cutting, milling or other machining process, or other processes) and can have a constant width, or can have a varying width as described in greater detail below.

Figure 5B:
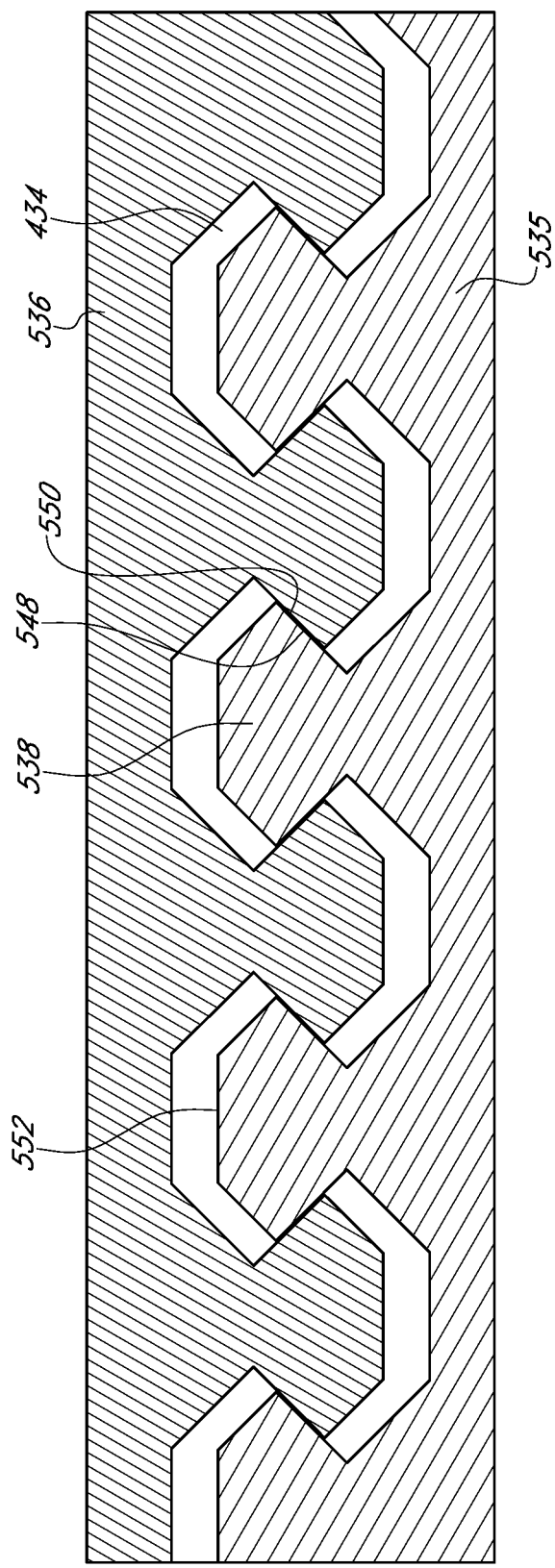
FIG. 5B is a partial enlarged side view showing the relief features of the instrument shaft of FIG. 4 in a tensioned configuration.

The relatively narrower width $W_N$ of the neck portion 542 as compared to the widths $W_H$ and $W_B$ of the head portion 544 and base 540 defines angled portions 548 and 550 that are oriented at an acute angle relative to a longitudinal axis $A_L$ (FIG. 3) of the shaft 305. Referring now to FIG. 5B, a view of the complementary interlocking engagement members 538 in interlocking engagement is shown. Such conditions are associated with a tension side of the shaft 305 (FIG. 3) when the shaft 305 is bent to a predetermined bend angle. As shown in FIG. 5B, the angled portions 548 and 550 of the complementary interlocking engagement members interlock with one another and prevent any further relative axial movement of the opposite sides 535 and 536 along the longitudinal axis $A_L$ of the shaft 305 (FIG. 3).

Figure 5C:
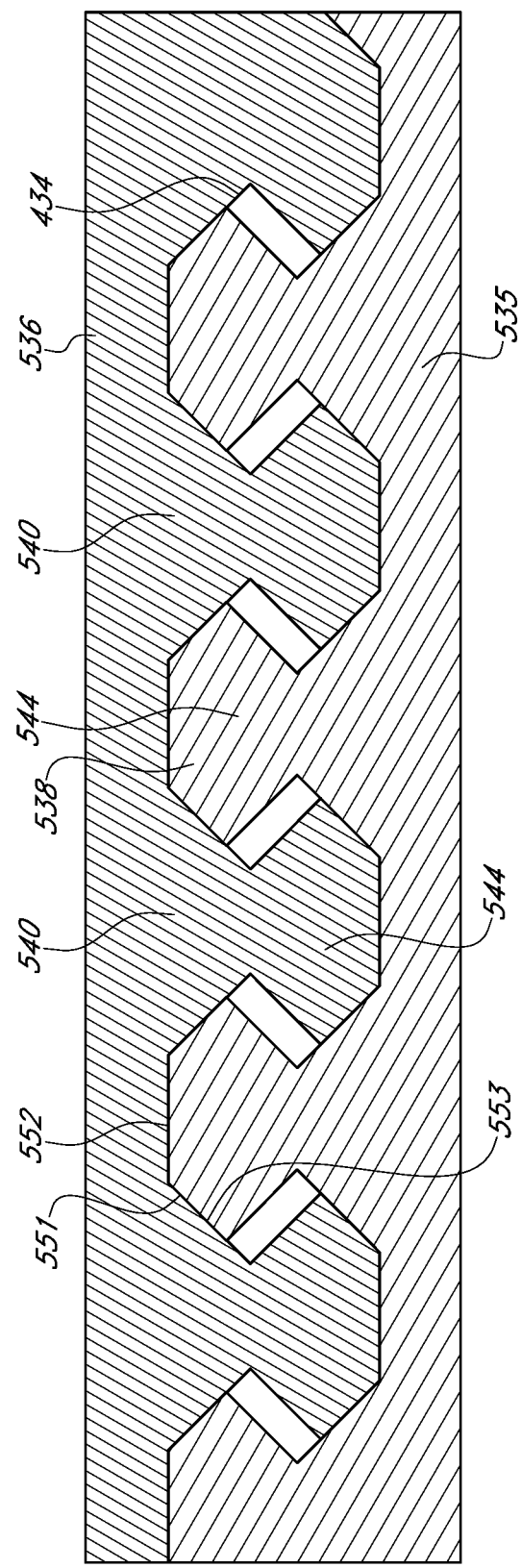
FIG. 5C is a partial enlarged side view showing the relief features of the instrument shaft of FIG. 4 in a compressed configuration.

Referring now to FIG. 5C, a view of the complementary interlocking engagement members 538 in engagement conditions associated with a compression side of the shaft 305

(FIG. 3) when the shaft 305 is bent to a predetermined angle is shown. As shown in FIG. 5C, each head portion 544 contacts the opposite side (i.e., opposite sides 535 and 536) between neighboring bases 540, thereby preventing further relative axial movement of the opposite sides 535 and 536 along the longitudinal axis $A_L$ of the shaft 305.

As shown in FIGS. 5B and 5C, the configuration of the relief feature 434 permits relative movement between the complementary interlocking engagement members 538 within a range of angles up to a predetermined bend angle, thereby enhancing the flexibility of the shaft 305 (FIG. 3) within the range of angles up to the predetermined bend angle. Once the predetermined bend angle is achieved, the contact between the complementary interlocking engagement members 538 on compression and tension sides of the shaft as shown in FIGS. 5B and 5C prevents further movement, enabling the shaft portions including the relief features to exhibit axial stiffness generally equal to the axial stiffness of the shaft portions that do not include relief features. In some embodiments, the predetermined bend angle corresponds to a bend angle obtained by the shaft when the instrument is installed in a manipulator system, such as in the configuration of instruments 104, 106 and manipulator 100 of FIG. 1. Such bend angles may be, for example, in the range of up to 10 degrees, in the range of up to 20 degrees, or other ranges. In one exemplary embodiment, the bend angle required to install the shaft in the manipulator is about 5 degrees.

Further, the predetermined bend angle may encompass a range of predetermined bending angles of the shaft. For example, various factors such as manufacturing tolerances and variations in material characteristics may result in the complementary interlocking engagement members engaging at slightly different bend angles depending on the rotational orientation and external forces applied to the shaft. Thus, while shafts of the present disclosure are described as engaging at a predetermined angle, a person of ordinary skill in the art would understand that such a predetermined angle is subject to normal variation, and the predetermined angles discussed herein are accordingly subject to variations resulting from such factors.

In addition to providing axial stiffness as described above, the relief features can be configured to exhibit rotational stiffness generally equal to the rotational stiffness of the shaft portions that do not include relief features. For example, when the shaft is bent to a predetermined bend angle, the complementary interlocking engagement features defined by the relief feature can be configured to engage one another to prevent rotational movement between the complementary interlocking engagement features.

For example, as shown in FIG. 5C, the angled portions 551 and 553 engage one another on the compression side of the shaft 305 (FIG. 3). In order to ensure the angled portions 551 and 553 engage on both sides of the complementary interlocking engagement features, the gap 546 (FIG. 5A) is wider along faces 552 of the head portions 544 relative to the width of the gap 546 along angled portions 550 and 548. The size of the gap 546 along the head portions 544 relative to the gap 546 along the angled portions 548, 550, 551, and 553 can be determined by the angle formed between the angled portions 550 and the gap along the faces 552. For example, in the embodiment of FIGS. 5A-5C, the angled portions 551, 553 are formed at an angle of 45 degrees relative to the other portions of the gap 546. To ensure that the angled portions 551 and 553 fully engage with one another, the size of the gap 546 along faces 552 is equal to the gap 546 between the angled portions 551, 553 divided by the cosine of the angle of 45 degrees. As a non-limiting example, if the gap 546 between the angled portions 550 is 0.001" (0.0254 mm), the gap between the non-angled portions is 0.001"/cos(45°) =0.0014" (0.036 mm). The additional gap width in the non-angled portions ensures that the angled portions 550 engage one another fully when the predetermined bend angle is achieved to reduce or preclude relative rotation between the opposing sides 535 and 536.

Other angles subtended by the angled portions relative to the non-angled portions are contemplated, and thus other relative differences between the gap between the angled portions and the gap between the non-angled portions is within the scope of the disclosure. Further, if the gap 546 along the faces 552 is made even greater than the gap 546 between the angled portions 551, 553 divided by the cosine of the angle, the faces 552 will not "bottom out" between the head portions 544, but the angled portions 551, 553 will engage one another and will prevent rotational and axial relative movement between the opposing sides 535 and 536.

In other embodiments, the width of the gap 546 can optionally be consistent throughout the relief feature. In such embodiments, and when the pattern of the relief feature is otherwise generally similar to the configuration of FIGS. 5A-5C, the end of the head portion 544 will make contact with the shaft body between adjacent base portions before the angled portions 550 contact one another, thereby allowing some degree of rotational compliance even when the predetermined bend angle is achieved. However, in some applications, the rotational compliance introduced by the equal-width gap may be sufficiently small so as to not significantly compromise the function of the shaft and associated instrument. Further, the equal-width gap may be less costly to manufacture than the varied width gap described above and may thus have economical benefit for applications in which a small amount of rotational compliance is acceptable.

Figure 6A:
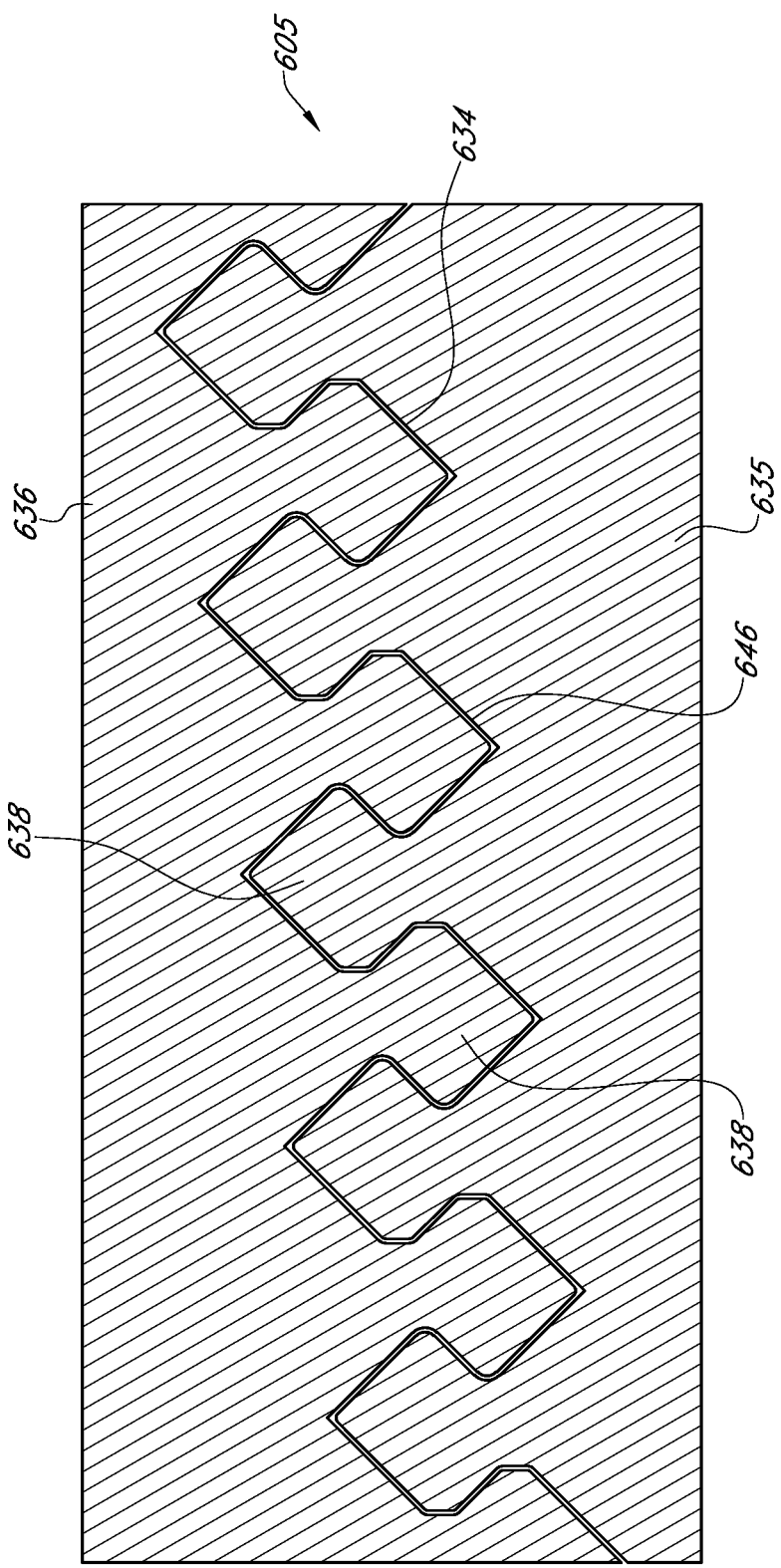
FIG. 6A is a partial enlarged side view of an instrument shaft with relief features in a neutral configuration according to another exemplary embodiment of the disclosure.

Referring now to FIG. 6A, another embodiment of a shaft 605 with a relief feature 634 according to the present disclosure is shown. Similar to the embodiment of FIGS. 5A-5C, the relief feature 634 is configured to preclude rotational movement (e.g., twisting movement) of opposing sides 635 and 636 relative to one another when the shaft 605 is bent to a predetermined bend angle. As shown in FIG. 6A, the relief feature 634 defines generally diamond-shaped complementary interlocking engagement members 638. The relief feature 634 defines leading angled portions 648 on each of the complementary interlocking engagement members 638 that contact corresponding portions of opposing sides 635 and 636 when the shaft 605 is bent to a predetermined angle as discussed in greater detail below. Unlike the embodiment shown in FIGS. 4-5C, the relief feature 634 does not include any portions that extend within a plane normal to a longitudinal axis of the shaft 605, and a gap 646 defining the relief feature 634 has a uniform width throughout the relief feature 634.

Figure 6B:
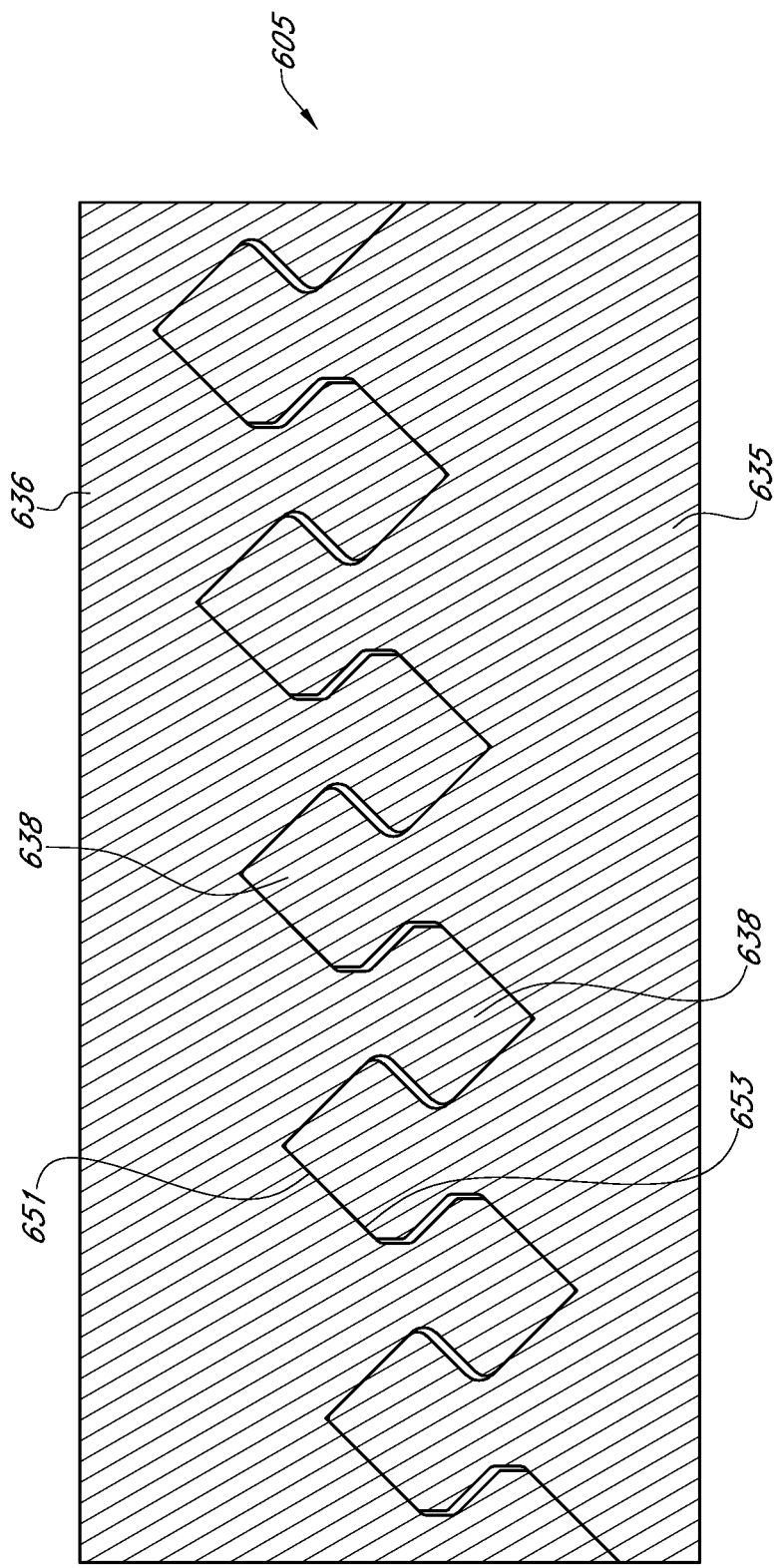
FIG. 6B is a partial enlarged side view of the instrument shaft of FIG. 6A with the relief features in a compressed configuration.
Figure 6C:
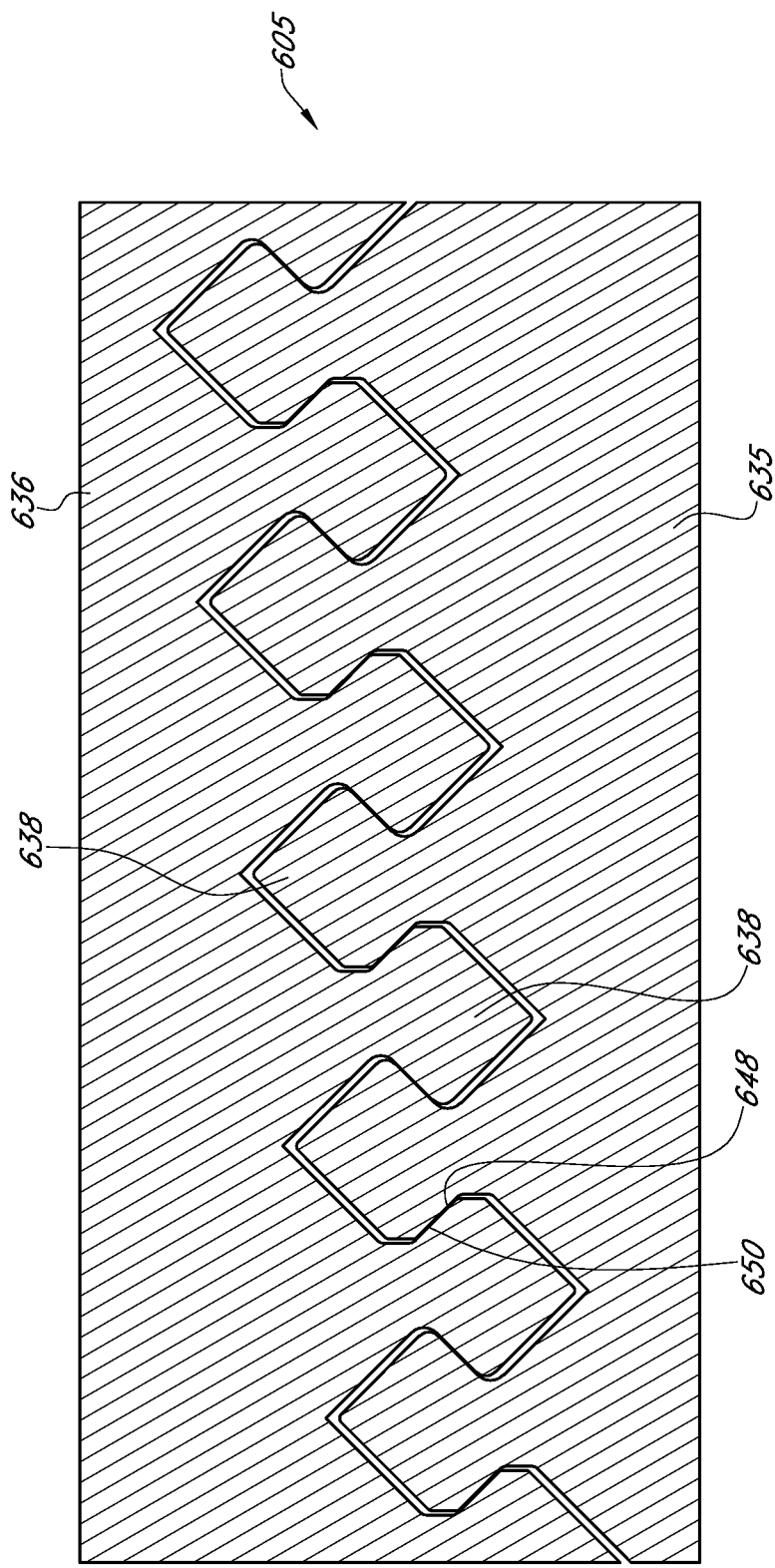
FIG. 6C is a partial enlarged side view of the instrument shaft of FIG. 6A with the relief features in a tensioned configuration.

FIG. 6B shows the complementary interlocking engagement members 638 in an engagement condition associated with a compression side of the shaft 605 when the shaft 605 is bent to a predetermined angle. Angled portions 651 and 653, which form non-orthogonal angles with respect to a longitudinal axis (e.g., axis $A_L$ shown in FIG. 3) of the shaft 605, engage as the opposing sides 635 and 636 are brought together, thereby precluding relative rotation between the opposing sides 635 and 636 on the compression side of the shaft 605. Similarly, with reference now to FIG. 6C, on the tension side of the shaft 605, the angled portions 648 and 650 of the complementary interlocking engagement members 638 on the opposing sides 635 and 636 of the shaft 605 engage one another to preclude relative rotation of the opposing sides 635 and 636 once the shaft 605 reaches a predetermined bend angle, similar to the embodiment of FIGS. 4-5C discussed above.

Figure 7:
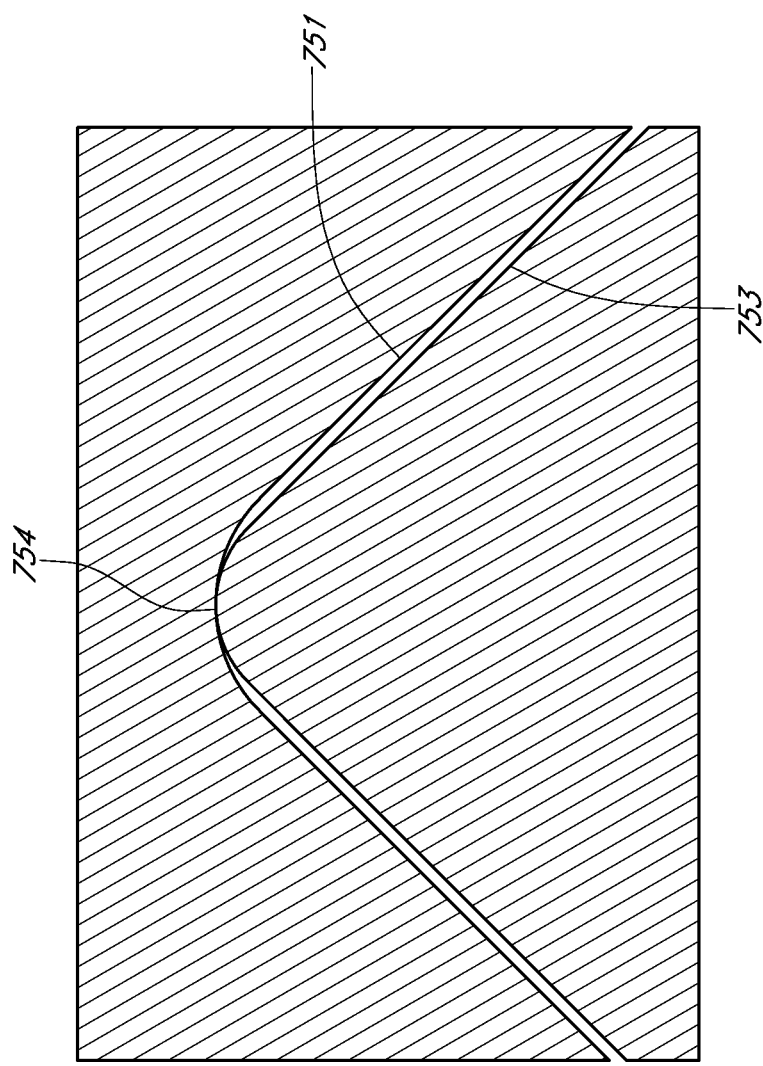
FIG. 7 is a partial enlarged side view of a relief feature according to another exemplary embodiment of the present disclosure.

In order to ensure that the angled portions 651 and 653 engage one another fully on the compression side of the shaft 605 when the shaft 605 is bent to a predetermined angle, the relief feature 634 can include a relieved area at a location where the angled portions 651 and 653 come together. FIG. 7 provides an illustration of why angled portions 751 and 753 may not fully engage one another to preclude rotational backlash of the shaft in the absence of such a relieved area. A configuration in which the gap 646 is equal throughout the relief feature 634 would result in a point contact or nearly point contact at contact area 754, as shown in FIG. 7, while the angled portions 751 and 753 are still separated by a gap. Such a configuration could result in rotational backlash when the shaft is rotated.

Figure 8:
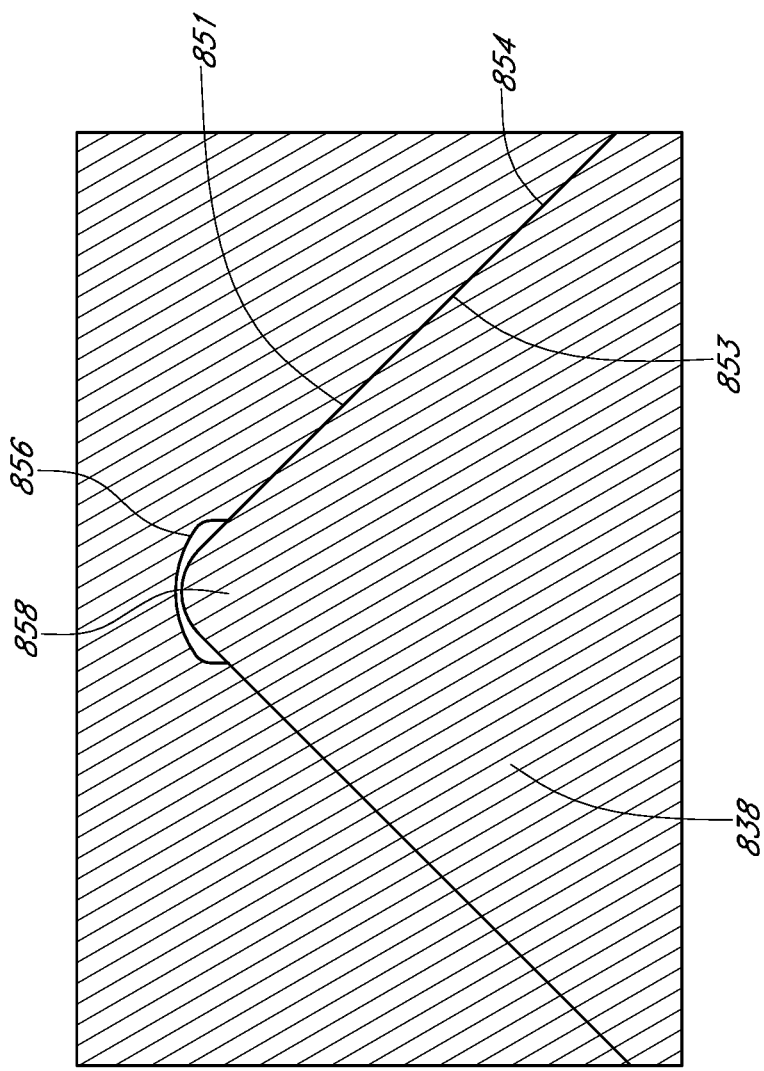
FIG. 8 is a partial enlarged side view of a relief feature according to another exemplary embodiment of the present disclosure.

Referring now to FIG. 8, an exemplary embodiment in which a relief feature 834 is provided with a relieved area 854 is shown. In the embodiment of FIG. 8, the relief feature 834 includes a relieved area 856 that provides space for a tip 858 of the complementary interlocking engagement feature 838 between the leading angled portions 848, enabling the angled portions 851 and 853 to engage as shown in FIG. 8 and prevent rotational backlash when the interlocking engagement members are interlocked.

Figure 9:
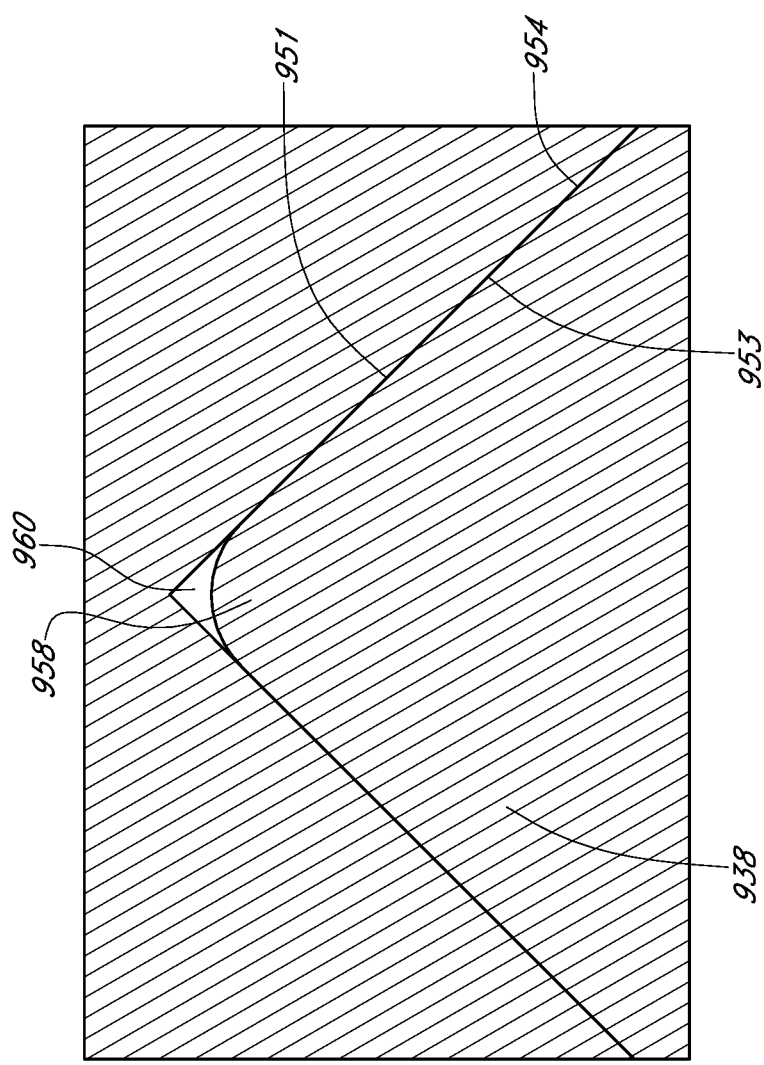
FIG. 9 is a partial enlarged side view of a relief feature according to another exemplary embodiment of the present disclosure.

FIG. 9 shows another exemplary embodiment of a relief feature 934. In this embodiment, a tip 958 of the complementary interlocking engagement feature 938 between angled portions 951 and 953 is radiused to a greater degree than a corresponding recess 960 into which the tip is received. As shown in FIG. 9, this arrangement similarly enables full contact of the angled portions 951 and 953 to preclude rotational backlash of the shaft.

The embodiments of FIGS. 8 and 9 are exemplary and non-limiting, and any configuration that enables substantial contact of the angled portions 651, 851, 951, and 653, 853, and 953 is within the scope of the disclosure. In addition, as discussed above in connection with the embodiment of FIGS. 3-5C, some degree of rotational compliance can potentially be acceptable as a tradeoff for reduced manufacturing cost that may be realized with a gap having a constant width, such as a laser cutting tool or other tool used to form the relief feature in the shaft. Thus, although FIG. 7 is shown and described herein mainly to illustrate the advantages provided by the embodiments of FIGS. 8 and 9, the embodiment of FIG. 7 is also an embodiment that could potentially be used where such a degree of rotational compliance is acceptable in return for lesser manufacturing costs.

Additionally, under sufficient axial loading of the embodiment of FIG. 7, plastic deformation of the tip of the shaft portion at contact area 754 can optionally be induced until the angled portions 751 and 753 contact one another. After such plastic deformation occurs, the angled portions 751 and 753 function similarly to angled portions 851, 853 and 951, 953 discussed above in connection with FIGS. 8 and 9, in that angled portions 751 and 753 engage one another on a compression side of the bent shaft to mitigate (e.g., eliminate) rotational backlash in the shaft. In this way, i.e., by subjecting the shaft of FIG. 7 to axial loading sufficient to plastically deform the tip portions, the manufacturing cost saving of equal-width reliefs can be realized along with the backlash prevention afforded by other designs including reliefs having varied width.

In embodiments generally like the embodiment described in connection with FIGS. 3-5C, some degree of rotational backlash may exist in the shaft, particularly under conditions in which the shaft is bent to an angle less than the predetermined bend angle and, as a result, the angled portions (e.g., angled portions 548, 550, 551, and 553 in FIGS. 5A-5C) are not fully engaged with one another on the tension and compression sides of the shaft. Such backlash can be the result of a relief feature extending helically continuously around multiple turns of the shaft. Accordingly, some exemplary embodiments can include relief features that are configured to reduce (e.g., eliminate) backlash under any degree of bending from a zero-degree bend to the predetermined bend angle.

Figure 11:
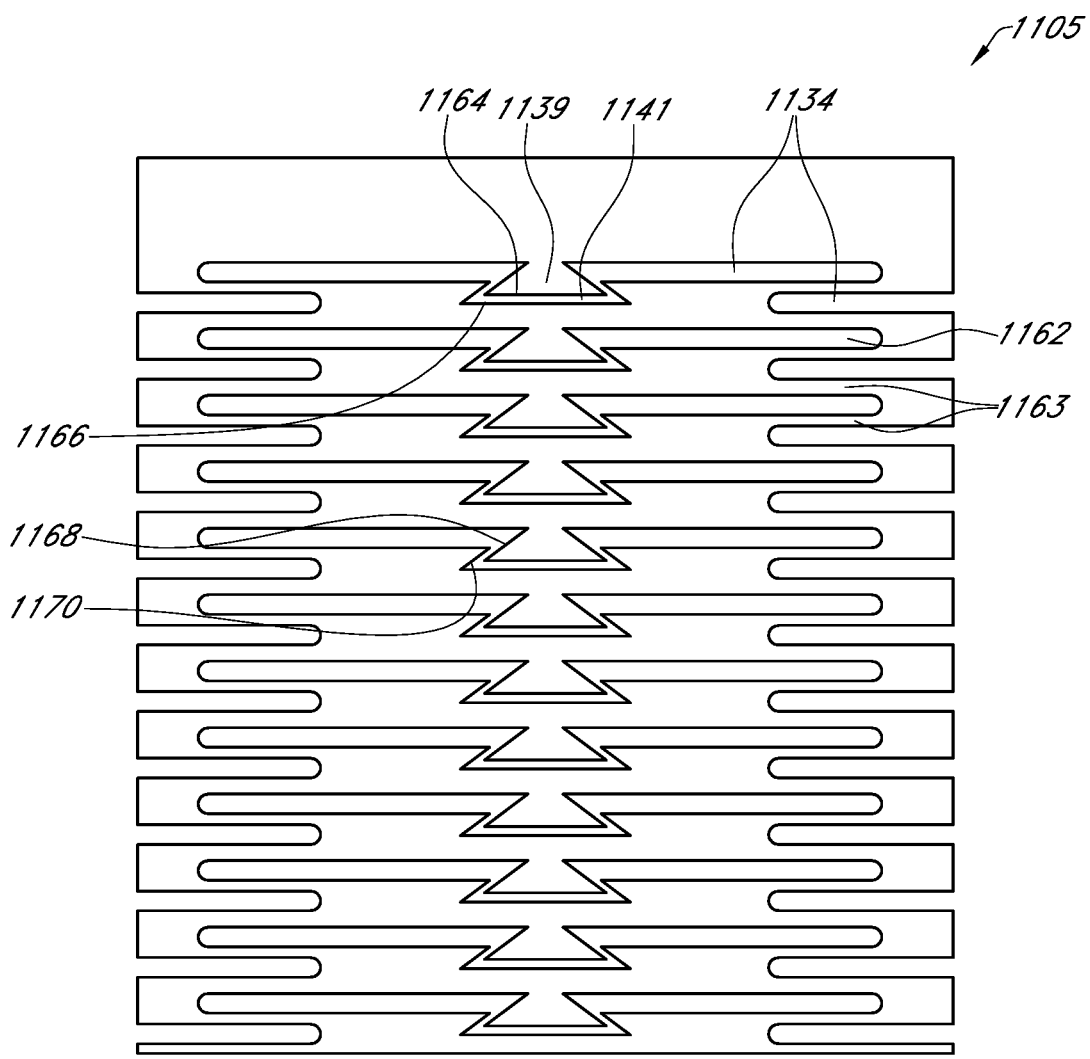
FIG. 11 is a partial enlarged side view of a relief feature according to another exemplary embodiment of the present disclosure.

Referring now to FIG. 11, another embodiment of shaft 1105 with a relief feature 1134 is shown. The shaft 1105 is shown with a 180° portion of the circumference of the shaft projected into the plane of FIG. 11. The relief feature 1134 includes multiple, unconnected reliefs 1162 that extend around less than a full circumference of the shaft 1105. As shown in FIG. 11, the multiple, unconnected reliefs 1162 extend in a non-helical direction lying in a plane normal to a longitudinal axis $A_L$ of the shaft 1105. Because none of the individual unconnected reliefs 1162 extend fully around the circumference of the shaft 1105, the unconnected reliefs 1162 do not introduce rotational backlash in the shaft. Material of the shaft 1105 remaining between the individual, unconnected reliefs 1162 can form flexural members 1163 that elastically deform as the shaft 1105 is bent. While the unconnected reliefs 1162 in the embodiment of FIG. 11 do not extend helically, in other exemplary embodiments, the unconnected reliefs could extend in a helical pattern, and/or other patterns, around the shaft 1105. Further, while the projection of FIG. 11 represents a 180° portion of the circumference of the shaft 1105, each of the unconnected reliefs 1162 can extend a lesser or greater extend around the shaft 1105 than is shown in the embodiment of FIG. 11.

As the shaft 1105 is bent to the desired angle, such as a predetermined bend angle as discussed above in connection with various other embodiments, the portions of the shaft 1105 defined by the unconnected reliefs 1162 (e.g., the flexural members 1163) may undergo elastic deformation and thus facilitate bending of the shaft 1105 to the desired angle. Further bending of the shaft 1105 could potentially result in plastic deformation of the shaft 1105 or otherwise compromise the structure and material of the shaft 1105. To prevent bending of the shaft 1105 beyond that permitted by elastic deformation of the shaft portions defined by the unconnected reliefs 1162, the relief feature 1134 can include engagement members 1139 that fit within pockets 1141 to prevent bending of the shaft 1105 beyond the predetermined bend angle. The engagement members 1139 and corresponding pockets 1141 function similarly to the interlocking engagement members 438, 538, 638 discussed above in connection with the embodiments of FIGS. 3-5C by engaging at the predetermined bend angle to prevent the shaft 1105 from being bent beyond the predetermined bend angle.

In the embodiment of FIG. 11, the relief features comprise two longitudinal rows of engagement members 1139 positioned diametrically opposite one another around the shaft 1105. To increase (e.g., maximize) axial stiffness of the shaft 1105 in use, the shaft 1105 can be oriented such that when a row of engagement members 1139 is positioned on the compression side of the shaft 1105, a base portion 1164 of each engagement member 1139 is in contact with a corresponding base portion 1166 of each pocket 1141 of the relief feature 1134. Likewise, angled portions 1168 of each engagement member 1139 can be configured to contact angled portions 1170 of each pocket 1141 on a tensioned side of the shaft 1105 to contribute axial stiffness to the shaft 1105 when the shaft 1105 is bent to the predetermined bend angle.

Figure 12A:
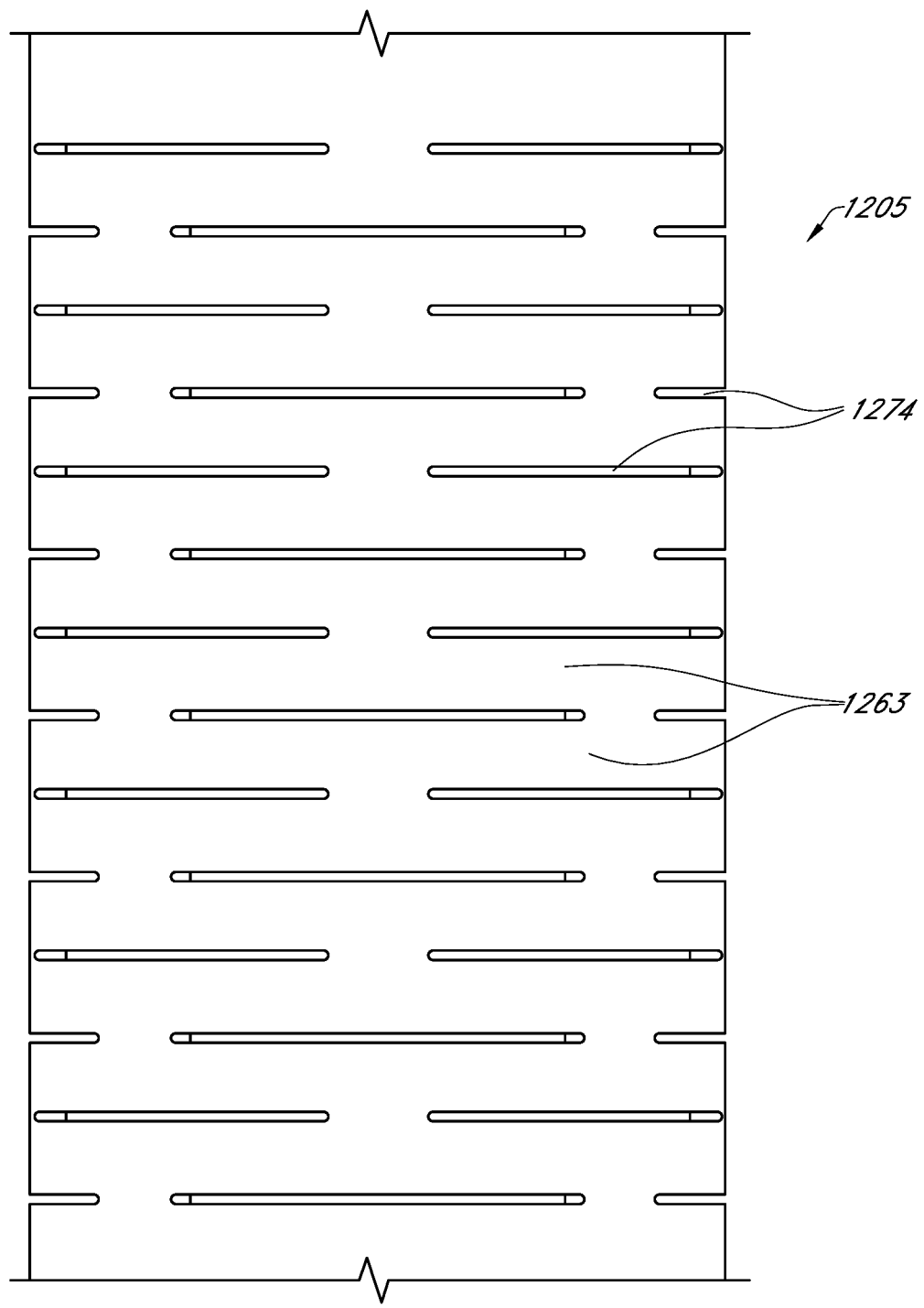
FIG. 12A is a partial enlarged side view of a shaft with a relief feature according to another exemplary embodiment of the present disclosure.

Referring now to FIG. 12A, another exemplary embodiment of a shaft 1205 with a relief pattern according to the present disclosure is shown. In the embodiment of FIG. 12A, the relief features comprise unconnected, radially cut reliefs 1274 that extend partially around the shaft 1205. The radially cut reliefs 1274 are placed in a pattern repeating in offset rows along a portion of the shaft 1205. In the example of FIG. 12A, the reliefs 1274 repeat 4 times around the circumference of the shaft 1205. Other embodiments can include a lesser or greater number of reliefs around the perimeter (e.g., circumference), and the number of reliefs around the perimeter (e.g., circumference) can be altered along with other variables such as length and width of the reliefs, spacing along the axis of the shaft 1205, and the total number of rows of reliefs can be chosen based on the desired properties of the shaft.

Similar to the exemplary embodiment of FIG. 11, material remaining between the reliefs 1274 form flexural members 1263 that can elastically deform to permit elastic bending of the shaft 1205 to a desired degree. Further, because the flexural members 1263 are coupled to one another in a continuous fashion, the shaft 1205 is enabled to transmit applied torque without excessive mechanical backlash.

Figure 12B:
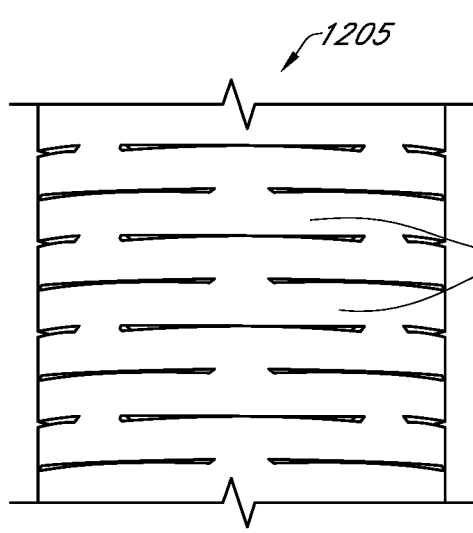
FIG. 12B is a partial enlarged side view of the shaft of FIG. 12A under an axial compressive load.

Referring now to FIG. 12B, a side view of shaft 1205 of FIG. 12A is shown in an axially compressed condition. Under sufficient axial compressive load, central portions of the flexural members 1263 deflect (e.g., move relative to one another) along the axial direction of the shaft 1205 until they contact one another. Mechanical contact (e.g., engagement) between the flexural members 1263 contributes to axial stiffness of the shaft 1205, once sufficient axial loading occurs to bring the flexural members 1263 into engagement with one another.

Figure 12C:
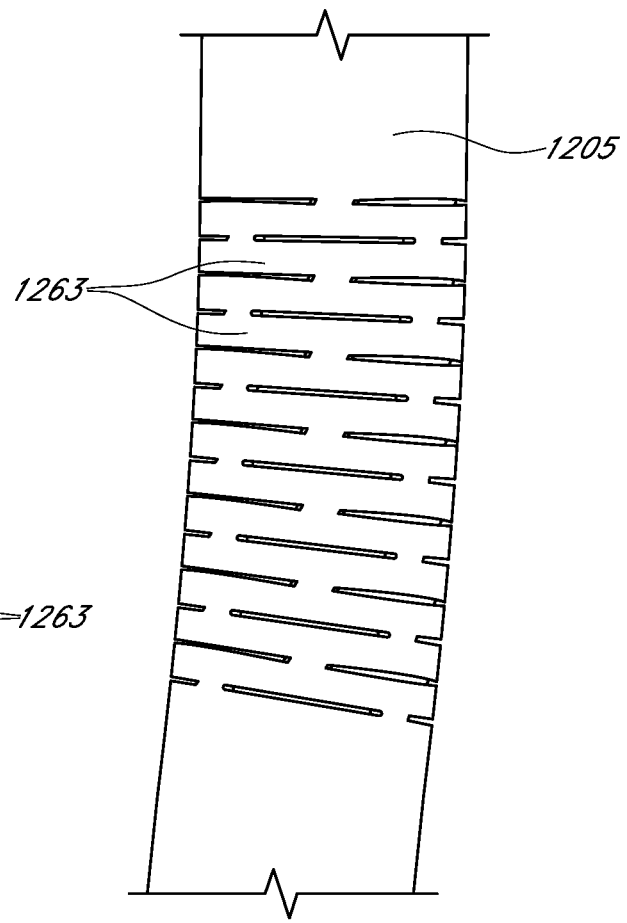
FIG. 12C is a side view of the shaft of FIG. 12A under a bending load.

Referring now to FIG. 12C, a side view of shaft 1205 of FIGS. 12A and 12B is shown in a bent condition. In the configuration of FIG. 12C, the left side (as viewed in FIG. 12C) of the shaft 1205 is under compression and the right side of the shaft 1205 is under tension. On the left side, the flexural members 1263 are brought into contact by a compressive force, while on the right side, the flexural members 1263 are separated further from one another by a tensile force. In this condition, contact between the flexural members 1263 on the compression side of the shaft contribute to a relatively high axial stiffness of the shaft 1205. Because the embodiment of FIGS. 12A-12C does not use interlocking features like other embodiments disclosed herein, resistance of the shaft 1205 to plastic deformation in tension, compression, and/or torsion is limited by the material characteristics of the shaft 1205 such as elastic modulus, tensile strength, and compressive strength. Likewise, while the shaft 1205 may not be susceptible to mechanical backlash due to the continuous nature of the flexural members 1263, elastic and/or plastic deformation of the shaft 1205 in torsion can potentially occur depending on the magnitude of applied loads.

Relief features according to the present disclosure can provide various additional advantages. For example, many surgical instruments are subjected to autoclave environments to clean and sterilize the instruments for reuse. The high temperatures experienced by the instrument can result in thermal expansion of components such as the shaft, and expansion of the shaft in turn can generate undesirable tension in components that extend through the shaft, such as tension cables or rods for actuation of a wrist or end effector. Surgical instrument shafts with relief features according to the present disclosure, when not bent to the predetermined maximum angle, can exhibit a total length shorter than a corresponding shaft without the relief features, because in a straight configuration, the relief features of the shaft collapse equally around the circumference of the shaft, thereby reducing the shaft length from an effective "in use" length. Further, some instruments with conventional shafts require additional mechanisms to release tension on actuation elements when the instruments are removed from the associated manipulators, and instrument shafts of the present disclosure could eliminate the need for such mechanisms, thereby reducing weight, cost, and complexity of the instrument.

Instruments including the embodiments described herein may be used, for example, with remotely operated, computer-assisted surgical systems employing robotic technology such as, for example, with a DA VINCI® Surgical System, such as the DA VINCI SI® Surgical System or the DA VINCI XI® Surgical System, Da Vinci SP, and Ion, both with or without Single-Site® single orifice surgery technology, all commercialized by Intuitive Surgical, Inc. of Sunnyvale, California Although various embodiments described herein are discussed with regard to surgical instruments used with a manipulating system of a computer-assisted surgical system employing robotic technology, the present disclosure is not limited to use with surgical instruments for such surgical systems. For example, various embodiments described herein can optionally be used in conjunction with hand-held, manual or semi-automated surgical instruments, such as those used for manual laparoscopic surgery, or other surgical and non-surgical instruments.

This description and the accompanying drawings that illustrate exemplary embodiments should not be taken as limiting. Various mechanical, compositional, structural, electrical, and operational changes may be made without departing from the scope of this description and the invention as claimed, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with the following claims being entitled to their fullest breadth, including equivalents, under the applicable law.

What is claimed is:

1. An instrument, comprising:
   a tubular shaft;
   an end effector coupled to a distal end portion of the tubular shaft; and
   relief features in a wall of the shaft and extending circumferentially and along at least a portion of a length of the shaft, the relief features having a pattern defining complementary engagement features on opposing sides of the relief features, each of the complementary engagement features comprising a base portion having a first width, a neck portion having a second width less than the first width, and a head portion having a third width greater than the second width;
   wherein
   the complementary engagement features each comprise a first angled portion tapering in a straight line between and connecting the base portion and the neck portion and a second angled portion flaring in a straight line between and connecting the neck portion and the head portion,
   the complementary engagement features move relative to one another in response to bending of the shaft, and
   the complementary engagement features engage one another on one or both of tension and compression sides of the shaft on a condition that the shaft is bent to an angle within a predetermined range of bend angles.

2. The instrument of claim 1, wherein the pattern defining the complementary relief features extends generally in a helical pattern around a circumference of the shaft along at least a portion of the shaft.

3. The instrument of claim 1, wherein the relief features form a plurality of rings spaced along a length of the shaft.

4. The instrument of claim 1, wherein, on the condition the shaft is in a straight configuration, the relief features comprise a gap between the complementary engagement features.

5. The instrument of claim 4, wherein a width of the gap varies along the relief features.

6. The instrument of claim 1, wherein the second width is less than the first width and the third width.

7. The instrument of claim 1, wherein each first angled portion tapers between the base portion and the neck portion.

8. The instrument of claim 1, wherein, on the condition that the shaft is bent to an angle within the predetermined range of bend angles, one or more of the head portions on a first of the opposing sides of the relief features engages with one or more base portions on a second of the opposing sides of the relief features.

9. The instrument of claim 8, wherein the complementary engagement features engage one another on one or both of the tension and compression sides of the shaft on the condition that the shaft is bent to an angle of 20 degrees or less.

10. The instrument of claim 9, wherein engagement of the head portions precludes relative rotation between complementary engagement features on opposing sides of the relief features.

11. The instrument of claim 1, wherein:
    the relief features in the shaft comprise a first set of relief features, and
    the shaft comprises a second set of relief features spaced from the first set of relief features along a longitudinal axis of the shaft.

12. The instrument of claim 1, wherein the relief features comprise a plurality of individual, unconnected reliefs extending in a plane normal to a longitudinal axis of the shaft.

13. The instrument of claim 1, wherein the pattern of the relief features comprises a helical pattern extending continuously around more than one circumference of the shaft.

14. The instrument of claim 1, wherein the head portion of each complimentary engagement feature comprises a third angled portion, the third angled portion tapering in a straight line to an apex of the head portion.

15. The instrument of claim 14, wherein the third angled portion terminates in a flat end portion of the head portion.

16. The instrument of claim 15, wherein, on the condition the shaft is in a straight configuration, the relief features comprise a gap between the complementary engagement features, wherein the gap comprises a first gap along the flat end portion of each head portion and a second gap along the second angled portion of each complementary engagement feature, wherein the first gap is wider than the second gap.

17. The instrument of claim 14, wherein the third angled portion terminates in a pointed end portion of the head portion.

18. A method of installing an instrument in a manipulator system, the method comprising:
bending a shaft of the instrument to within a range of predetermined bend angles,
wherein during the bending:
moving complementary engagement features defined by a pattern of relief features in a wall of the shaft relative to one another, the complementary engagement features comprising a base portion having a first width, a neck portion having a second width less than the first width, and a head portion having a third width greater than the second width, wherein the complementary engagement features each comprise a first angled portion tapering in a straight line between and connecting the base portion and the neck portion and a second angled portion flaring in a straight line between and connecting the neck portion and the head portion; and
engaging the complementary engagement features with one another on one or both of a tension side of the shaft and a compression side of the shaft on a condition that the shaft is bent to an angle within the range of predetermined bend angles.

19. The method of claim 18, wherein bending the shaft comprises inserting a distal end of the shaft through an instrument entry guide of the manipulator system.

\* \* \* \* \*